United States Patent [19]

Henderson

[11] 4,199,558

[45] Apr. 22, 1980

[54] TISSUE PROCESSING METHOD

[75] Inventor: Kenneth J. Henderson, Crowthorne, England

[73] Assignee: Shandon Southern Products Limited, Cheshire, England

[21] Appl. No.: 892,769

[22] Filed: Apr. 3, 1978

Related U.S. Application Data

[62] Division of Ser. No. 691,585, Apr. 7, 1976, Pat. No. 4,099,483.

[51] Int. Cl.² .......................... G01N 1/30; G01N 33/16
[52] U.S. Cl. ........................................................ 424/3
[58] Field of Search ................... 427/2, 4, 248; 424/3; 23/230 B; 118/48, 49, 429; 134/11, 21, 31; 34/22, 26, 11; 8/94.11

[56] References Cited

PUBLICATIONS

"Handbook of Histopathological and Histochemical Techniques", 3rd ed., Culling—Butterworth & Co., (1974), pp. 54, 55.

*Primary Examiner*—Morris Kaplan
*Attorney, Agent, or Firm*—Kurt Kelman

[57] ABSTRACT

Histological and like tissue specimens are processed by suspending them successively in the condensing vapors of a dehydrating fluid and a clarifying fluid and permeating the tissue specimens with the respective condensed fluid.

4 Claims, 1 Drawing Figure

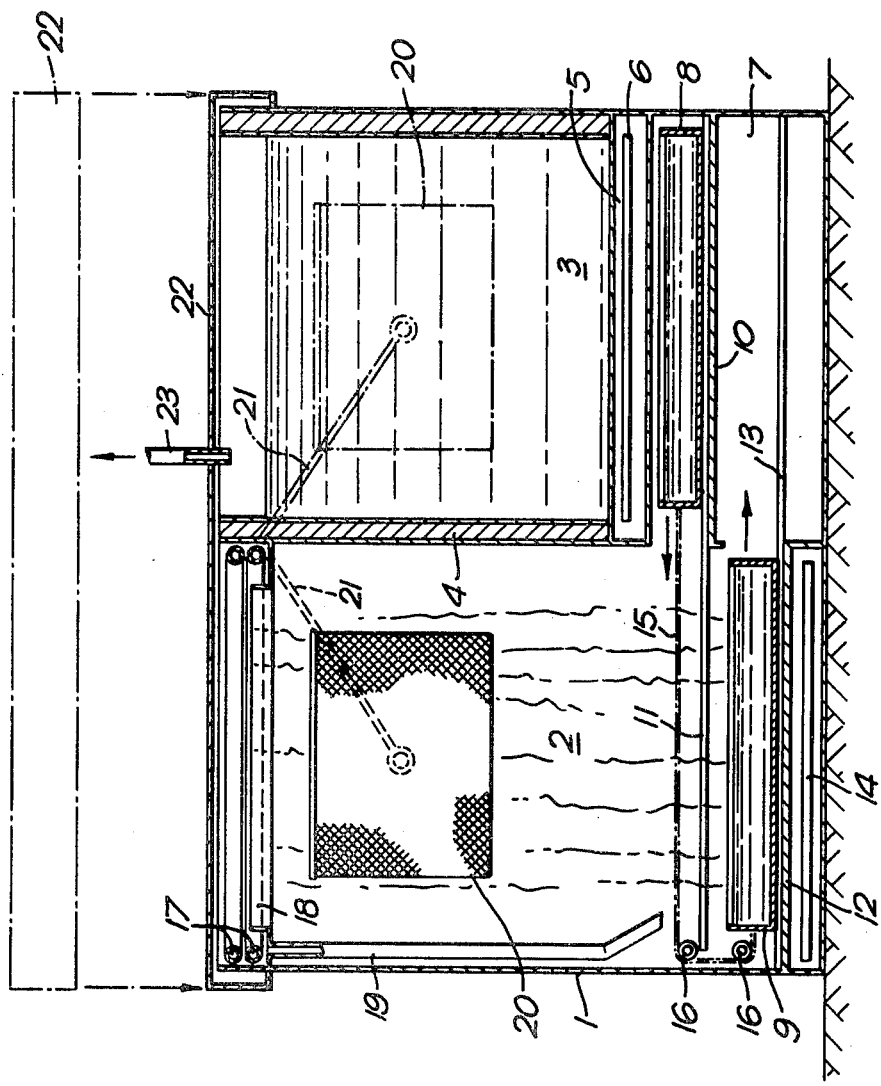

TISSUE PROCESSING METHOD

This is a division of application Ser. No. 691,585, filed Apr. 7, 1976, now U.S. Pat. No. 4,099,483.

FIELD OF THE INVENTION

This invention concerns processing of histological and like tissue specimens by suspending them in the condensing vapours of a volatile processing fluid.

SUMMARY OF THE INVENTION

In my parent U.S. Pat. No. 4,099,483, I have disclosed tissue processing apparatus which comprises a vessel defining a vapour space above a receptacle for volatile processing liquid, heating means for vaporising the volatile processing liquid in the receptacle and, near the upper end of the vapour space, means for effecting condensation of vapour in the upper part of the vapour space and for returning condensate to the receptacle.

The apparatus preferably includes at least two receptacles for different volatile liquids and means for bringing a selected receptacle into position for cooperation with the heating means; thus the vapour space may be selectively charged with the vapour of two or more different fluids.

This invention is particularly applicable to the treatment of tissue specimens sequentially with dehydrating and clearing agents (for instance with alcohol and xylene, respectively) in the stages preceding wax impregnation in the preparation of such specimens for sectioning, for example. Conventionally, tissue specimens are sequentially suspended for suitable periods of time, usually with agitation to ensure penetration of the tissue by the liquid, in each of a series of baths of dehydrating agent (e.g. alcohol) of progressively increasing concentration, whereafter the specimens are immersed in one or more successive baths of clearing agent (e.g. xylene) and finally in a bath of molten wax until impregnated therewith. In the present invention tissue specimens may be suspended in to the condensing vapours of the respective liquids for suitable periods of time.

To facilitate subsequent impregnation of the specimens with wax, the apparatus includes a wax bath and means for transferring the specimens from the vapour space to the wax bath. The transferring means includes an openwork basket adapted to hold tissue specimens to be processed, the basket being suitably carried by suspension means to transport the basket between the vapour space and the wax bath.

In order that the vapour space may be conveniently charged with condensing vapour at a suitable temperature, the apparatus includes suitable means for sealing at least the vapour space to enable the atmospheric pressure within the vapour space to be adjusted to raise or lower the vaporisation temperature of the volatile liquid to a desired value. For instance, in the case of processing tissue specimens sequentially with alcohol and xylene and vapour space may be held at a temperature of, say 65° C., the boiling point of alcohol under normal atmospheric pressure so that processing of the tissue specimens with alcohol vapour in the vapour space may be accomplished with normal atmospheric pressure therein, processing in a subsequent stage with xylene, for instance, being accomplished under an atmospheric pressure within the vapour space of 610 mm Hg at which its boiling point is reduced to 65° C. from its value of 138° C. at normal pressure. If toluene were to be used as the clearing agent instead of xylene in this example, the pressure in the vapour space would be reduced to 660 mm Hg to reduce the boiling point of the toluene to 65° C. from its normal pressure value of 110° C. By such means tissue specimens may be processed at a constant temperature with condensing vapours of substances that boil at different temperatures under normal atmospheric pressure.

Preferred apparatus comprises a vessel divided into two side-by-side compartments by a partition that defines on one side a wall of a vapour space and on its other side a wall of a wax bath, the bottom of the latter being at a level above the bottom of the vapour space so as to provide, beneath the wax bath, accommodation space for volatile liquid receptacles out of use at any instant. A slide rail arrangement provides support for two or more receptacles for volatile liquids and a transport mechanism enables the receptacle containing a selected liquid to be withdrawn from this accommodation space and positioned in the vapour space for vaporisation of liquid in that receptacle by heat from the said heating means that may, for instance, be an electrical heater suitably positioned at the bottom of the vapour space for cooperation with the selected receptacle.

Conveniently the upper end of the vapour space is provided with a tube coil through which a coolant, e.g. cold water, may be circulated to cause condensation of vapour at the level of this coil, a trough being provided adjacent to the wall of the vapour space below the tube coil to catch condensate falling from the coil, and a drainpipe extending from this trough to a suitable position serving to return such condensate to the receptacle in the vapour space.

THE DRAWING AND DESCRIPTION OF PREFERRED EMBODIMENT

An embodiment of an apparatus for carrying out the method of the invention is illustrated, partly diagrammatically, in the FIGURE of the accompanying drawing that is a sectional elevation of tissue processing apparatus constituting such embodiment.

The illustrated tissue processing apparatus comprises a vessel 1 divided into two side-by-side compartments, namely a vapour space 2 and a wax bath 3, by a partition 4. The bottom of the wax bath 3 is defined by a bottom plate 5 fitted with an electrical heating element 6 and disposed at a level above the bottom of the vapour space 2 so as to provide, beneath the wax bath, accommodation space 7 in which either of two receptacles 8, 9 may be located when it is out of use. The accommodation space 7 is divided by a platform 10 that provides a support for slide rails 11 extending across the lower part of the vapour space 2 and on which the receptacle 8 is movable between its out of use position in the accommodation space 7 as shown in the drawing and a position within the vapour space 2.

The bottom of the vapour space 2 has a platform 12 that supports slide rails 13 extending into the accommodation space 7 below the platform 10 and on which receptacle 9 is slidable between the position shown and an out of use position in the accommodation space 7.

The platform 12 encloses an electrical heating element 14 that serves to heat the platform 12 and to cause this to heat, by radiation, the receptacle 8 or 9 when either of these is positioned above the platform 12 within the vapour space 2.

Movement of the receptacles 8 and 9 on their respective slide rails 11 and 13 is conveniently co-ordinated so that the movement of one receptacle into the accommodation space 7 is accompanied by movement of the other from the space 7 into position in the lower part of the vapour space 2. The drawing illustrates a flexible linkage 15 connecting the receptacles 8 and 9, and extending over pulleys 16 so that movement of either receptacle into the accommodation space 7 causes the other to be withdrawn from the accommodation space 7 into position in the vapour space 2. The means for moving the receptacles 8, 9 are not shown and may take any convenient form: draw lines (not shown) extending through the wall of the accommodation space 7 would provide for direct manual movement of the receptacles whereas a linkage connecting the righthand ends of the two receptacles, as seen in the drawing, and passing over suitable pulley or sprocket means would provide for movement of the receptacles by rotary movement of such pulley or sprocket, as by manual operation of a knob connected thereto, or powered operation by means of a suitable motor.

The apparatus further includes a tube coil 17 arranged near to the walls of the upper end of the vapour space 2 and above a trough 18 that serves to catch condensate falling from the tube coil in operation of the apparatus. The trough 18 is fitted with at least one drain tube 19 for conducting condensate from the trough to a point in the lower part of the vapour space 2 where condensate discharged from the tube may fall into the receptacle 8 or 9, as the case may be, that is positioned in the space 2 over the platform 12.

The apparatus further includes an openwork basket 20 that is supported by a pivoted arm 21 (the details of which are not shown) that may be swung from a position in which the tissue basket 20 is suspended within the upper part of the vapour space 2 (as shown in full lines) to the alternative position indicated in broken lines and within the wax bath 3.

The apparatus further includes a lid 22 adapted to fit sealingly on the upper end of the vessel 1 to seal both the vapour space and the wax bath from the external atmosphere when desired. The lid 22 is fitted with a connection 23 by means of which a vacuum pump or a pressure pump may communicate with the interior of the vessel to evacuate or pressurise the latter to a desired internal atmospheric pressure.

In use of such apparatus, tissue specimens to be dehydrated and wax impregnated are placed in the basket 20 that is then positioned in the vapour space 2. One of the receptacles 8, 9 and containing a suitable dehydrating agent, e.g. alcohol, is moved out of the accommodation space 7 and into position in the lower part of the vapour space 2 to be heated by the heater 14 and platform 12 so that the dehydrating agent is caused to boil gently and fill the vapour space with its vapour. A coolant, e.g. cold water, is circulated through the tube coil 17 so that vapour at the top of the vapour space 2 condenses and is collected in the trough 18 to flow from the latter via the drain tube(s) 19 back to the receptacle 8 or 9 as the case may be. The dehydrating agent vapour also condenses on the basket 20 and on tissue specimens therein to penetrate the tissue and displace moisture retained therein.

Following immersion in the dehydrating agent vapour for a suitable period, the receptacle containing the dehydrating agent is moved into the accommodation space 7 so that the other receptacle, containing a clearing agent such as xylene, is moved from the accommodation space into position in the lower part of the vapour space 2. The clearing agent is thereby brought to the boil and fills the vapour space with its vapour that thereby contacts the specimens in the basket 20. The clearing agent penetrates the tissue and displaces the dehydrating agent absorbed during the preceding dehydration stage.

Following exposure of the tissue specimens to the clearing agent vapour for a suitable period of time, the lid 22 is removed and the tissue basket 20 swung from its position within the vapour space 2 to its alternative position within the wax bath 3 to effect impregnation of the tissue specimens with molten wax contained in the wax bath.

If, as will usually be the case, the dehydrating agent (e.g. alcohol) and the clearing agent (e.g. xylene) have different boiling points at atmospheric pressure, the temperature within the vapour space may be held at the same value, or at similar values, during both the dehydration and clearing stages by suitable adjustment of the atmospheric pressure within the vessel when changing over from dehydration to clearing. Thus, for instance, dehydration with alcohol may be accomplished at about 65° C. with ambient atmospheric pressure within the vessel while clearing by treatment with xylene may be accomplished at about the same temperature by reduction of the internal atmospheric pressure within the vessel to about 610 mm mercury.

An advantage accruing from the use of the invention, as compared with conventional methods in which specimens are immersed in the corresponding liquids, is that in the dehydration step the tissue specimens are exposed only to the pure dehydrating agent, water and other materials extracted from the tissue being carried away from the latter with the liquid returning to the dehydrating agent bath to be retained therein. If desired a dessicant may be provided within the vapour space 2 to absorb water vapour and to minimise dilution of the dehydrating agent in the relevant receptacle. In conventional tissue processing with immersion of the tissue specimens in a series of dehydrating agent baths of increasing concentration, the baths become contaminated by matter extracted from the specimens so that an extended immersion period is required to compensate for the progressive dilution and contamination of the baths and to effect full dehydration. Thus with the method of the invention shorter processing periods are feasible.

It has been observed that shrinkage of specimens exposed to dehydrating and clearing agents in the vapour phase is no greater than that caused by immersion of such specimens in liquid baths as in conventional tissue processing.

I claim:

1. A method of processing a tissue specimen, comprising the steps of suspending the specimen in condensing vapours of a volatile dehydrating agent, condensing the vapours on the specimen, and permitting the condensed vapours of the dehydrating agent to penetrate throughout the specimen and to be absorbed thereby until the moisture therein has been completely displaced.

2. The method of claim 1, wherein the dehydrated specimen is suspended in condensing vapours of a clearing agent and the condensed vapours of the clearing agent are permitted to penetrate through the dehydrated specimen until the dehydrating agent has been displaced.

3. The method of claim 2, wherein the specimen is successively suspended in the vapours of the dehydrating agent and of the clearing agent boiling at the same temperature to produce the respective vapours.

4. The method of claim 1, comprising the further step of adjusting the atmospheric pressure wherein the specimen is suspended to cause the agent to vapourize at a selected temperature.

* * * * *